United States Patent [19]
Stauner et al.

[11] 3,978,122
[45] Aug. 31, 1976

[54] ACYLUREA COMPOUNDS

[75] Inventors: Thomas Stauner; Rolf Kyburz, both of Marly, Switzerland

[73] Assignee: Ciba-Geigy AG, Basel, Switzerland

[22] Filed: May 2, 1974

[21] Appl. No.: 466,323

[30] Foreign Application Priority Data
May 7, 1973   Switzerland.......................... 6429/73

[52] U.S. Cl. .............................. 260/553 E; 96/111;
260/117; 260/465 H; 260/465 K
[51] Int. Cl.$^2$........................................ C07C 127/22
[58] Field of Search............ 260/553 E, 117; 96/111

[56] References Cited
UNITED STATES PATENTS

| | | | |
|---|---|---|---|
| 3,106,468 | 10/1963 | Burness................................. | 96/111 |
| 3,455,893 | 7/1969 | Froehlich.......................... | 96/111 X |
| 3,574,709 | 4/1971 | Froehlich .................... | 260/553 E X |
| 3,641,116 | 2/1972 | Froehlich .................... | 260/553 E X |
| 3,687,698 | 8/1972 | Cohen............................... | 96/111 X |
| 3,851,013 | 11/1974 | Perrey et al.................. | 260/553 E X |

OTHER PUBLICATIONS

"Polymethylenebis (acroyloxyethylurea) . . . ", Iwekura et al., CA 49: P4015g (1954).

*Primary Examiner*—Daniel E. Wyman
*Assistant Examiner*—Thomas A. Waltz
*Attorney, Agent, or Firm*—Joseph G. Kolodny; Edward McC. Roberts; Prabodh I. Almaula

[57]  ABSTRACT

The present invention relates to the new compounds of the formula

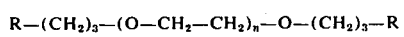

wherein $n$ is an integer having a value of 1 to 100 and R represents a radical of the formula Cl—H$_2$C—CH$_2$—CO—NH—CO—NH— or preferably H$_2$C=CH—CO—NH—CO—NH—. The new compounds are useful for crosslinking hydrophilic colloids such as gelatine, particularly for crosslinking gelatine layers in photographic material.

4 Claims, No Drawings

ACYLUREA COMPOUNDS

The invention relates to the new acylurea compounds of the formula

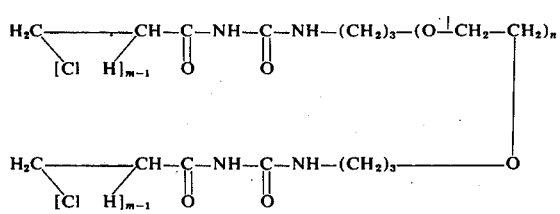

wherein $m$ is 1 or 2 and $n$ is an integer having a value of 1 to 100. If $m$ is 2, the compounds contain two β-chloropropionic acid radicals ($ClH_2C-CH_2-CO-$). In general, the compounds with two acrylic acid radicals ($H_2C=CH-CO-$), that is to say the compounds of the formula (1) wherein $m$ is 1, are particularly valuable.

Further compounds to be signaled out are those of the formula (1) of which the polyglycol chain is not very long, for example possesses fewer than 40 $-(O-CH_2-CH_2)-$ groups. Here there may especially be mentioned the compounds of the formulae

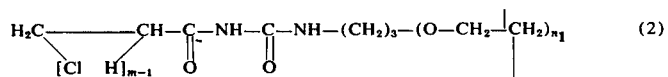

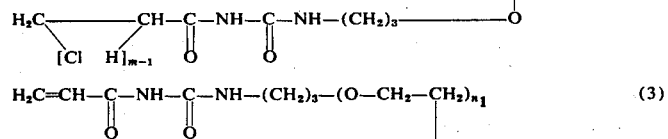

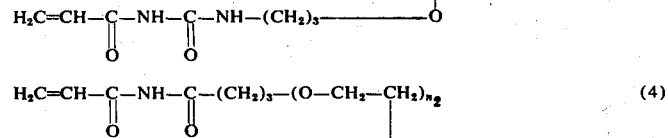

wherein $n_1$ denotes an integer having a value of 1 to 10 and $n_2$ denotes an integer having a value of 1 to 5.

The compounds of the formulae (1) to (4) can readily be prepared in accordance with the reaction sequence shown below:

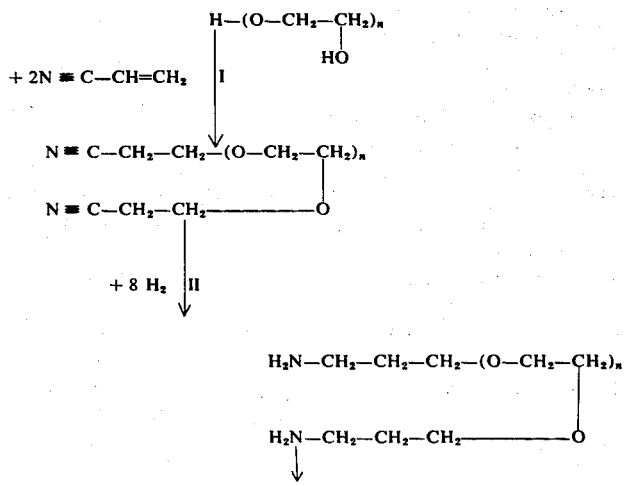

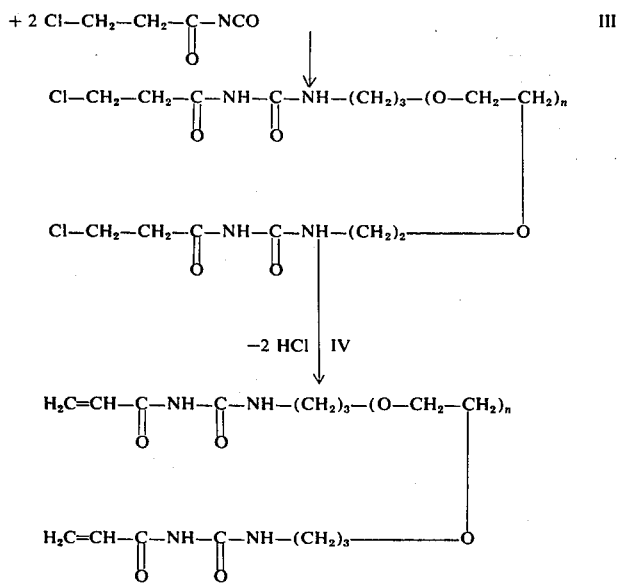

As can be seen from the above comments, ethylene glycol or lower polyethylene glycols with 2, 3, 4 or 5 —(CH$_2$—CH$_2$—O)— groups are preferably used for the preparation of the acyl compounds in reaction stage I. Polyethylene glycols of higher molecular weight, for example 300, 400, 600, 1,000, 1,450, 1,500, 1,550, 2,000, 3,000 or 4,000, can also be used. It is also possible to start from mixtures of different glycol compounds, which will above all be of relevance in the case of the higher polyethylene glycols since the commercially available products are as a rule mixtures of this type, with a greater or lesser scatter of the quoted average molecular weight.

The crosslinking agents used according to the invention can be employed in the textile industry and leather industry, the manufacture of paper, the plastics industry, the glue industry and the gelatine industry. Above all, they are used as hardeners for water-soluble polymers such as polyvinyl alcohol, gelatine or gelatine derivatives, especially in the form of layers, containing such colloids, of photographic materials. The reaction of these colloids with these compounds in general takes place easily and in the usual manner. The compounds are as a rule sufficiently water-soluble.

In most cases it suffices to add the products to be used according to the invention, as an aqueous solution or in a solid form which is as finely divided as possible, to an aqueous solution of the hydrophilic colloid with good stirring.

It is thus possible, for example, to bring together a solution of the crosslinking agents in water, or in water mixed with, for example, ethanol, methanol or acetone, with the colloids at normal or slightly elevated temperature. Gelatine, which optionally contains silver halide and/or other components required for the production of photographic images, has proved particularly suitable for this purpose. The gelatine can, in the usual way, be cast on a base to form a layer, and can be dried. The layer can then be left at elevated temperature or at room temperature for a certain period, for example up to 24 hours. In the course thereof, hardening takes place rapidly and progressively; the melting point of the gelatine is raised substantially, for example by 25° to 60°C, and the reciprocal swelling factor increases correspondingly (compare Table 1).

The amount of the hardener used depends on the desired degree of hardening but is suitably 0.1 to 10 percent by weight, based on the weight of the dry gelatine.

A particular advantage of the present crosslinking agents is that when they are used in low concentration they impart an adequate degree of hardness to the gelatine layers in as little as, for example, 24 to 48 hours, so that the castings can be tested by processing the samples immediately following their preparation, even at elevated temperature or in chemically aggressive processing baths.

It is a further advantage that in the hardening according to the invention, using the compounds of the formula (1), no significant change in pH in the emulsion layer occurs.

The hardening effect itself is very stable; even after prolonged storage at temperatures around 40°C and at a relative atmospheric humidity of about 70% no decrease in the reciprocal swelling factor is in general to be observed.

The degree of hardening is also not significantly changed by acids or bases even on prolonged exposure thereto, and this indicates that the hardener-gelatine bond has great resistance to hydrolysis.

The compounds used according to the invention are in addition generally sufficiently soluble in water and are very stable in aqueous solutions at low and medium pH values.

The good stability and adequate solubility are both particularly important properties which, for example, decisively determine the ability to use the compounds in photographic technology. Thus, for example, it is particularly desirable, for the continuous manufacture of photographic materials, that batches of solutions of crosslinking agents should remain stable at room temperature for several hours or days and that the concentration of the hardener, and hence its ability to crosslink gelatine, should not decrease or should only decrease insignificantly. On the other hand, it is equally important, for the same reason, that there should only be an insignificant, if any, decomposition or reaction with water of the hardener in the casting solution at about 40°C during the requisite standing time and dwell time, so as to maintain the full crosslinking action of the hardener over the course of several hours during casting, drying and storage of the photographic material.

Furthermore, the viscosity of the casting solution should not increase significantly during the standing time, as a result of the addition of the hardener. It is furthermore particularly important that the hardener should cause no yellowing, fogging or effect on the gradation even on prolonged treatment of the cast layer at fairly high temperature and atmospheric humidity.

The compounds of the general formula (1) meet these strict requirements with regard to stability to hydrolysis particularly successfully.

The hardeners are suitable for hardening (crosslinking) the most diverse layers containing gelatine, such as, for example, intermediate layers, emulsion layers, base layers, coating layers, backing layers and antihalation layers. The layers can not only contain the crosslinking agents but also additives of the most diverse kind, such as, for example, silver halide, pigments such as barium sulphate, titanium dioxide or silicon dioxide or organic pigments, such as coloured pigments, as well as image dyestuffs, colour coupling agents, sensitisers, filter dyestuffs, anti-halation dyestuffs and screen dyestuffs, stabilisers, UV absorbers, optical brighteners, crosslinking agents, lubricants, antistatic agents, latices or additional crosslinking agents.

Particularly in the case of compounds of relatively low molecular weight it is possible, because of their good diffusibility in a multi-layer material, to add them only to the auxiliary layers in order to achieve, through diffusion, a hardening of the adjoining silver halide layers.

These new crosslinking agents can also be used as mixtures with other compounds suitable for the crosslinking of water-soluble colloids, especially of gelatine.

EXAMPLE 1

33.6 g (0.2 mol) of 1,2-bis-($\beta$-cyanoethoxy)-ethane are dissolved in a mixture of 400 ml of tetrahydrofurane and 120 ml of water. 6 g of Raney nickel are added whilst stirring and a solution of 30.4 g (0.8 mol) of sodium borohydride in 100 ml of 8 N potassium hydroxide solution and 180 ml of water is allowed to run in dropwise, whilst keeping the temperature at between 20° and 25°C over the course of the reduction. The reaction is allowed to take place until no further hydrogen is evolved. The tetrahydrofurane layer is then separated from the aqueous layer in a separating funnel. The aqueous part is washed with 90 ml of tetrahydrofurane and the two tetrahydrofurane solutions are combined and dried over sodium carbonate. The solvent is evaporated off in vacuo, 300 ml of benzene are added to the residue, the insoluble component is filtered off and the benzene is again distilled off. The residue is distilled in a high vacuum, whereupon 1,2-bis-(3-amino-propoxy)-ethane (product of reaction II, n = 1) passes over at 88° to 91°C/0.26 mbar. 21.5 g are obtained.

100 ml of absolute acetonitrile are initially introduced into a flask equipped with a stirrer, thermometer, calcium chloride tube and two dropping funnels and are cooled to between −5° and −10°C. 26.4 g (0.15 mol) of the bis-(3-aminopropoxy)-ethane obtained are dissolved in 180 ml of absolute ether in one of the dropping funnels; in the second dropping funnel, 40 g (0.3 mol) of $\beta$-chloropropionyl isocyanate are dissolved in 180 ml of absolute ether.

These two solutions are now added dropwise in equivalent amounts, over the course of one hour, to the acetonitrile taken initially, whilst stirring well and keeping the temperature at −5° to −10°C. After the addition, the reaction mixture is allowed to warm to room temperature and the white precipitate is filtered off. The solvent is dissolved in 600 ml of boiling ethanol and the solution is allowed to crystallise. The crystallisation is repeated one more in the same way. After drying in a vacuum cabinet, 42.5 g of the product of reaction III (formula (2), $m = 2$, $n_1 = 1$, compare also Table 1, No. 6) of melting point 126° to 128°C are obtained.

40 g (0.09 mol) of the bis-chloropropionyl compound thus obtained are dissolved in 750 ml of absolute acetone at 50°C. 6 g of hydroquinone are added and the solution is cooled to 0°C.

20.05 g (0.198 mol) of triethylamine are added thereto and the mixture is stirred for 8 hours at room temperature. The triethylammonium chloride which has separated out is then filtered off and the solvent is evaporated off in vacuo at 30°C. The residue is suspended in 50 ml of water and the product is extracted with twice 40 ml of chloroform. The extract is dried over potassium carbonate and the solvent is distilled off. The resulting oil is recrystallised three times from a mixture of 400 ml of ethyl acetate/ether (1:1) with the addition of a little active charcoal. After drying in vacuo, 23.2 g of the product of reaction IV (formula (3), $m = 1$, $n_1 = 1$, compare Table 1, No. 1) of melting point 98° to 100°C are obtained.

EXAMPLE 2

1,350 g (0.4 mol) of bis-($\beta$-cyanoethoxy)-diethyl ether are diluted with 1,600 ml of absolute tetrahydrofurane and hydrogenated, together with 450 g of liquid ammonia and 130 g of Raney cobalt catalyst for 4 hours in an autoclave at 100°C and 120 bars. After the absorption of hydrogen has ceased, the catalyst is filtered off. The solvent is distilled off under normal pressure and the residue is fractionated in a high vacuum.

1,217 g (boiling point 115° to 116°/0.065 mbar, yield 87%) of 1,13-diamino-4,7,10-trioxatridecane of the formula

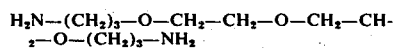

are obtained.

328 ml (3.2 mols) of 3-chloropropionyl isocyanate are initially introduced into 3 l of toluene and 330 g (1.5 mols) of 1,13-diamino-4,7,10-trioxatridecane are then added gradually. The reaction product which has separated out is filtered off and is recrystallised from methanol (Table 1, compound No. 7). Yield: 620 g (85%). Melting point: 95°C.

585 g (1.2 mols) of the 3-chloropropionylurea obtained are dissolved in 2.5 l of acetone and 426 ml of triethylamine are added. After 15 hours, the triethylammonium chloride which has precipitated is filtered off. About half the solvent is removed in vacuo and 1.2 l of ether are added. On intense cooling, the acryloylurea (Table 1, compound No. 2) crystallises out as a white powder. Yield: 423 g = 85%, melting point 63°–66°C.

EXAMPLE 3

Analogously to the instructions given in Example 2, and starting from the dinitriles from reaction I, it is possible to prepare, via reaction sequence II and III: the compounds of the formula (2) wherein m = 2 and $n_1$ = 3, 4 or about 33, that is to say No. 8, 9 and 10 of Table 1).

Elimination of hydrogen halide (reaction IV) leads to the compounds of the formula (3), wherein $n_1$= 3,4 or about 33 (see No. 3, 4 and 5 of Table 1).

EXAMPLE 4

In the examples which follow, the reciprocal swelling factor is used as a measure of the hardening. The samples are prepared as follows: 6 ml of a 6% strength gelatine solution, 1 ml of a 1% strength aqueous solution of the dyestuff of the formula 1 ml of an 0.025 molar hardener solution and 5 ml of deionised water are mixed and adjusted to pH = 6.5. The solution is poured onto a 13 cm × 18 cm triacetate film. After solidifying at 10°C, the product is dried over the course of one hour at 20°C. The dyestuff merely serves to make the samples more readily visible during the swelling measurements. The materials are stored at room temperature (normal storage: 18° to 22°C, 50% relative atmospheric humidity) or climatically controlled conditions (climatically controlled storage, 42° to 44°C, 69% relative atmospheric humidity).

To determine the reciprocal swelling factor, a thin section of 20μ is prepared from each of the samples and measured under a microscope. The thickness of the dry gelatine layer is then determined, deionised water is then added and after 4 minutes the thickness of the swollen gelatine layer is measured. The reciprocal swelling factor 1/SF corresponds to the following ratio:

$$1/SF = \frac{22 \text{ Thickness of the dry layer}}{\text{Thickness of the swollen layer}}$$

The results are summarised in Table 1; in these, $R_1$ denotes the radical of the formula $H_2C{=}CH{-}CO{-}NH{-}CO{-}NH{-}$ and $R_2$ the radical of the formula $Cl{-}H_2C{-}CH_2{-}CO{-}NH{-}CO{-}NH{-}$.

In the case of the compounds with the radical $R_1$, in particular, the climatically controlled storage does not impair the degree of crosslinking of the gelatine. Alkaline processing baths are also as a rule unable to exert an unfavourable influence on the degree of crosslinking. This applies in particular also to colour developers when processing chromogenic material.

TABLE 1

| No. | Crosslinking agent of the formula | 1/SF under normal storage after | | | 1/SF under climatically controlled storage after | |
|---|---|---|---|---|---|---|
|  |  | 3 hours | 2 days | 7 days | 2 days | 7 days |
| 1 | $R_1{-}(CH_2)_3{-}O{-}CH_2{-}CH_2{-}O{-}(CH_2)_3{-}R_1$ | 0.112 | 0.179 | 0.211 | 0.329 | 0.326 |
| 2 | $R_1{-}(CH_2)_3{-}(O{-}CH_2{-}CH_2)_2{-}O{-}(CH_2)_3{-}R_1$ | 0.109 | 0.147 | 0.192 | 0.353 | 0.364 |
| 3 | $R_1{-}(CH_2)_3{-}(O{-}CH_2{-}CH_2)_3{-}O{-}(CH_2)_3{-}R_1$ | 0.045 | 0.126 | 0.204 | 0.326 | 0.322 |
| 4 | $R_1{-}(CH_2)_3{-}(O{-}CH_2{-}CH_2)_4{-}O{-}(CH_2)_3{-}R_1$ | 0.058 | 0.138 | 0.209 | 0.293 | 0.361 |
| 5 | $R_1{-}(CH_2)_3{-}(O{-}CH_2{-}CH_2)_{33}{-}O{-}(CH_2)_3{-}R_1$ | 0.117 | 0.237 | 0.290 | 0.331 | 0.308 |
| 6 | $R_2{-}(CH_2)_3{-}O{-}CH_2{-}CH_2{-}O{-}(CH_2)_3{-}R_2$ |  |  |  | 0.126 | 0.134 |
| 7 | $R_2{-}(CH_2)_3{-}O{-}(CH_2{-}CH_2{-}O)_2{-}(CH_2)_3{-}R_2$ |  |  |  | 0.195 | 0.250 |
| 8 | $R_2{-}(CH_2)_3{-}O{-}(CH_2{-}CH_2{-}O)_3{-}(CH_2)_3{-}R_2$ |  |  |  | 0.327 | 0.329 |
| 9 | $R_2{-}(CH_2)_3{-}O{-}(CH_2{-}CH_2{-}O)_4{-}(CH_2)_3{-}R_2$ |  |  |  | 0.227 | 0.268 |
| 10 | $R_2{-}(CH_2)_3{-}O{-}(CH_2{-}CH_2{-}O)_{33}{-}(CH_2)_3{-}R_2$ |  |  |  | 0.204 | 0.250 |

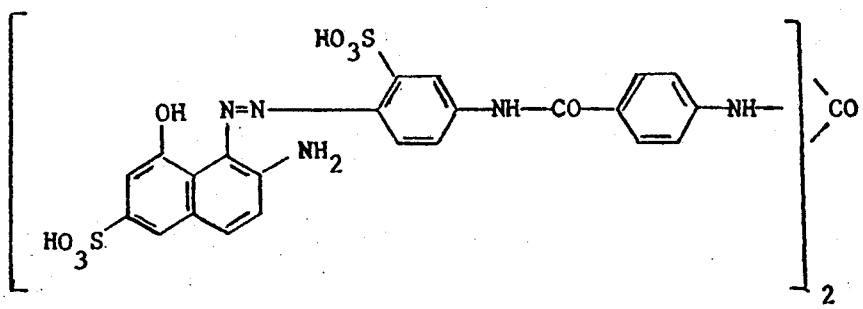

EXAMPLE 5

A silver halide emulsion containing 4% of iodide, 30 g of silver/kg and 80 g of gelatine/kg is cast, together with compound No. 2 of Table 1 as the crosslinking agent, onto a transparent base. TABLE 2 below shows the amounts of product and the results of the sensitometric examination after processing using a customary black-and-white processing method.

TABLE 2

| Crosslinking agent g/100 g of gelatine | Relative sensitivity log E | Gradation | Fogging |
| --- | --- | --- | --- |
| 0 | −0.31 | 1.98 | 0.05 |
| 2.9 | −0.26 | 1.45 | 0.05 |
| 5.8 | −0.24 | 1.46 | 0.03 |

The flattening of the gradation corresponds to the influence which crosslinking agents usually exert on photographic layers.

What we claim is:

1. An acylurea compound of the formula $$H_2C\diagdown_{[Cl\ H]_{m-1}}^{\diagup}CH-\underset{O}{\underset{\|}{C}}-NH-\underset{O}{\underset{\|}{C}}-NH-(CH_2)_3-(O-CH_2-CH_2)_n$$

$$H_2C\diagdown_{[Cl\ H]_{m-1}}^{\diagup}CH-\underset{O}{\underset{\|}{C}}-NH-\underset{O}{\underset{\|}{C}}-NH-(CH_2)_3-\!\!\!\!-O$$

wherein $m$ is 1 or 2 and $n$ denotes an integer having a value of 1 to 100.

2. An acylurea compound as claimed in claim 1 of the formula $$H_2C\diagdown_{[Cl\ H]_{m-1}}^{\diagup}CH-\underset{O}{\underset{\|}{C}}-NH-\underset{O}{\underset{\|}{C}}-NH-(CH_2)_3-(O-CH_2-CH_2)_n$$

$$H_2C\diagdown_{[Cl\ H]_{m-1}}^{\diagup}CH-\underset{O}{\underset{\|}{C}}-NH-\underset{O}{\underset{\|}{C}}-NH-(CH_2)_3-\!\!\!\!-O$$

wherein $m$ is 1 or 2 and $n_1$ denotes an integer having a value of 1 to 10.

3. An acylurea compound as claimed in claim 1 of the formula $$H_2C=CH-\underset{O}{\underset{\|}{C}}-NH-\underset{O}{\underset{\|}{C}}-NH-(CH_2)_3-(O-CH_2-CH_2)_n$$

$$H_2C=CH-\underset{O}{\underset{\|}{C}}-NH-\underset{O}{\underset{\|}{C}}-NH-(CH_2)_3-\!\!\!\!-O$$

wherein $n_1$ denotes an integer having a value of 1 to 10.

4. An acylurea compound as claimed in claim 1 of the formula $$H_2C=CH-\underset{O}{\underset{\|}{C}}-NH-\underset{O}{\underset{\|}{C}}-NH-(CH_2)_3-(O-CH_2-CH_2)_n$$

$$H_2C=CH-\underset{O}{\underset{\|}{C}}-NH-\underset{O}{\underset{\|}{C}}-NH-(CH_2)_3-\!\!\!\!-O$$

wherein $n_2$ denotes an integer having a value of 1 to 5.

* * * * *